United States Patent [19]

Jackman

[11] Patent Number: 4,642,385
[45] Date of Patent: Feb. 10, 1987

[54] PREPARATION OF MONOCHLOROPINACOLONE

[75] Inventor: Dennis E. Jackman, Prairie Village, Kans.

[73] Assignee: Mobay Corporation, Pittsburgh, Pa.

[21] Appl. No.: 799,540

[22] Filed: Nov. 19, 1985

[51] Int. Cl.$^4$ .............................................. C07C 45/63
[52] U.S. Cl. ..................................... 568/393; 548/262
[58] Field of Search ........................... 568/393; 548/262

[56] References Cited

U.S. PATENT DOCUMENTS

| 3,397,240 | 8/1968 | Kaufman et al. | 568/393 |
| 3,912,752 | 10/1975 | Meiser et al. | 548/262 |
| 4,196,150 | 1/1980 | Kraty et al. | 568/393 |
| 4,240,983 | 12/1980 | Schubart | 568/393 |
| 4,439,623 | 3/1984 | Krieger et al. | 568/393 |

Primary Examiner—James H. Reamer
Attorney, Agent, or Firm—Sprung Horn Kramer & Woods

[57] ABSTRACT

In the reaction of pinacolone with chlorine in a solvent to produce monochloropinacolone, the improvement which comprises employing a solvent such as an alcohol which contains HCl at the outset of the reaction whereby the amount of by-product dichloropinacolone produced is reduced.

6 Claims, No Drawings

PREPARATION OF MONOCHLOROPINACOLONE

The present invention relates to an improvement in the reaction of pinacolone with chlorine to produce monochloropinacolone.

German DOS No. 28 19 264 discloses the following synthesis, starting with pinacolone and ending up with the known herbicide N,N-dimethyl-N'-(5-t.-butyl-oxazol-3-yl)-urea:

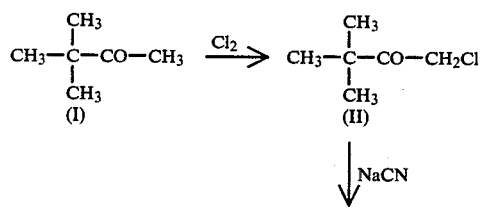

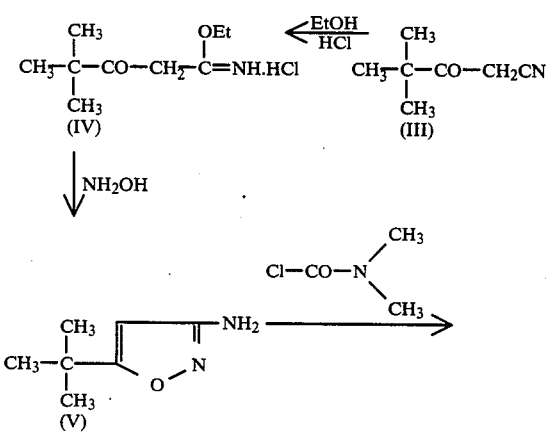

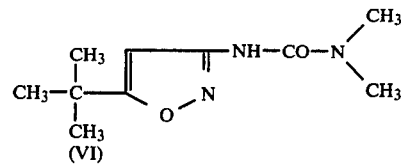

The process works moderately well and the monochloropinacolone II is produced in 92% yield and, after distillation, contains 0.3% of dichloropinacolone. Prior to such distillation our reproduction shows a dichloropinacolone content of about 4%, which is one reason for the distillation, i.e., to eliminate by-products which would interfere with the next step of the synthesis.

U.S. Pat. No. 3,912,752 discloses the following syntheses:

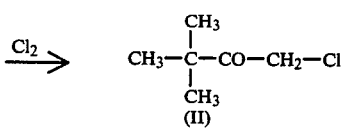

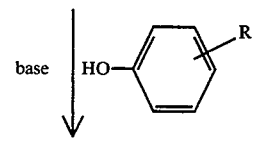

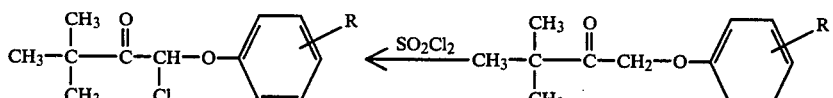

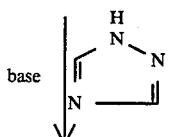

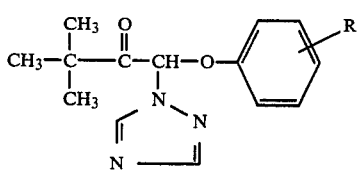

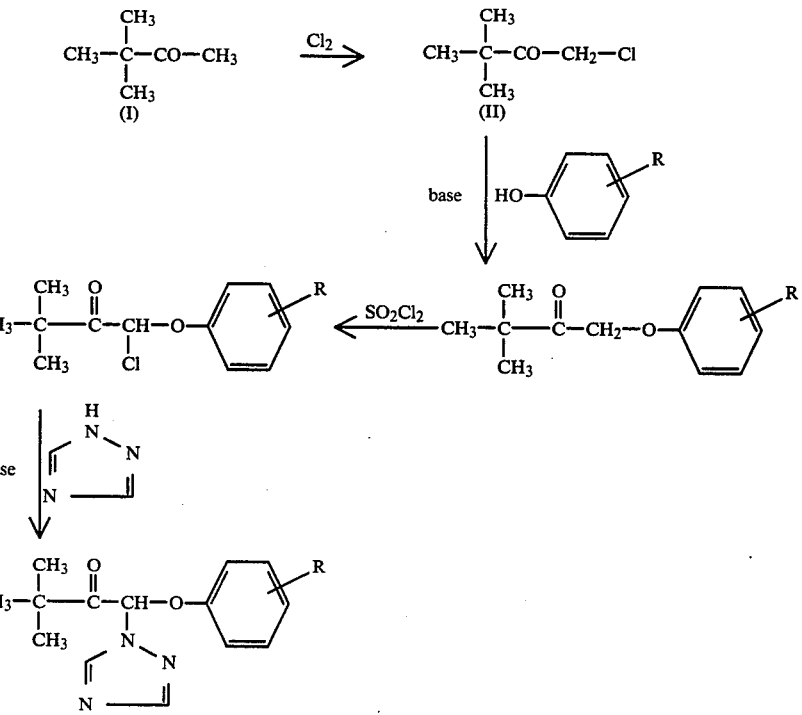

The products are known fungicides, R preferably being halogen, phenyl, phenoxy, halophenyl, halophenoxy, and the like. The products may be hydrogenated to convert the keto group to a carbinol, and those compounds are also fungicidal.

Here, too, dichloropinacolone in intermediate (II) reduces the yield in the subsequent steps. As a matter of fact, since dichloropinacolone has two chlorines to one in monochloropinacolone, the presence of dichloropinacolone results in a proportionately higher loss in the next step, e.g. 4% of dichloro in II will result in a next step product which might contain 8% of undesired bis-reaction product which is difficult to separate and thus goes through the further steps, contaminating the end product.

It is accordingly an object of the present invention to produce monochloropinacolone of such a purity that it can be directly used in further synthesis to give high yields without prior separation of impurities from the monochloropinacolone.

One by-product of the chlorination of pinacolone is HCl which remains dissolved in the solvent in which the chlorination is usually effected, e.g. an alkanol such as methanol. In distillation, prior to the vaporization of the monochloropinacolone the HCl will come off and is either permitted to escape or collected in water or other solvent which may contain an alkaline neutralizing agent. The reaction solvent comes off after the HCl and before the monochloropinacolone. The dichloropinacolone is least volatile and mostly stays behind as distillation residue.

In accordance with the present invention it has surprisingly been found that if the reaction solvent is not purified excessively before re-use but rather is re-cycled while still containing considerable HCl, in the next cycle the amount of dichloropinacolone by-product produced is so low that the monochloropinacolone need not be distilled but rather can be used directly in further reaction.

Stated otherwise, if the solvent contains HCl at the outset, pinacolone can be converted to monochloropinacolone with less than 1% of by-product dichloropinacolone. At the end of the reaction, the mass is boiled to vaporize the HCl and solvent which can then be used in another cycle, leaving behind a distillation residue of highly pure monochloropinacolone having only a low content of dichloropinacolone, so low as to permit direct use in further reaction.

For the first cycle, one can simply charge the solvent with HCl. While as little as about 100 mol % of HCl based on pinacolone gives the desired result, at least about 700 mol % is preferred and no disadvantage is seen to attend higher amounts up to saturation of the solvent. Since each cycle produces more HCl, eventually saturation will be reached except insofar as some HCl is stripped out of the solvent at the outset of solvent removal by distillation.

Suitable solvents for the chlorination are any liquid of moderate volatility and lower alkanols, especially methanol, are preferred. The ratio of solvent to pinacolone is not critical and a weight ratio of at least 5:1 is suitable. More solvent is permissible but must then be boiled off at the end of the reaction.

The chlorination is effected in known manner, preferably using chlorine gas as from a cylinder. The gas is advantageously bubbled into the HCl-containing solvent in which the pinacolone has been pre-dissolved. Temperatures of $-20°$ C. to room temperature are permissible but $-10°$ C. to $20°$ C. is preferred.

The reaction is generally carried out batchwise although one could add pinacolone incrementally as consumed. The reaction is somewhat exothermic and cooling is needed to maintain the desired temperature. If more than an equimolar amount of chlorine is provided, it will merely result in production of dichloropinacolone, an undesired by-product. If less than an equimolar amount of chlorine is provided, then there will be unreacted pinacolone which, if not recovered, would be wasted. However, there will be almost no dichloropinacolone formed, so a slight excess of pinacolone is preferred.

As noted, the monochloropinacolone distillation residue can be directly reacted further. In addition to the aforementioned syntheses of a herbicidal oxazolyl-urea, it can be used elsewhere wherever monochloropinacolone is needed.

The invention will be further described in the following illustrative examples wherein all parts are by weight unless otherwise expressed.

EXAMPLE 1

102 grams of pinacolone and 160 grams of methanol were charged to a flask and cooled to $-5°$ C. HCl gas was bubbled into the flask contents until saturation, the solution turning a dark yellow. 63 grams of chlorine were introduced into the solution, maintained at $-10°$ C. About 10 minutes after introduction of chlorine was completed, cooling was discontinued and the vessel was heated sufficiently to distill out methanol and excess pinacolone through an 8 inch Vigreaux column, thereby also removing HCl from the flask. The distillation residue comprised by weight 0.8 gram of unreacted pinacolone, 118 grams of monochloropinacolone and 1.2 grams of dichloropinacolone, corresponding to 1.0% of dichloropinacolone by weight based on the combined weights of monochloropinacolone and dichloropinacolone.

The recovered methanol was saturated with HCl and could then be directly reused in another run.

EXAMPLE 2

A series of runs was conducted under substantially the same conditions with varying amounts of HCl based on the starting pinacolone.

The amounts of reactants and end products and the ratio of desired and undesired end products are set forth in the following table:

| Pinacolone | HCl | Chloro Product, % by weight | | Wt. Ratio Mono/Di |
| --- | --- | --- | --- | --- |
| | | Mono- | Di- | |
| 100 g | 56.6 g | 95 | 3.0 | 33 |
| 100 g | 113.2 g | 95 | 1.5 | 64 |
| 100 g | 226.4 g | 95 | 1.1 | 85 |

EXAMPLE 3

Materials produced as in Example 2 were employed in known manner in accordance with the disclosure of U.S. Pat. No.3,912,752 to produce the known fungicide 1-(4-chlorophenoxy)-3,3-dimethyl-1-(1,2,4-triazol-1-yl)-butan-2-one by the following route

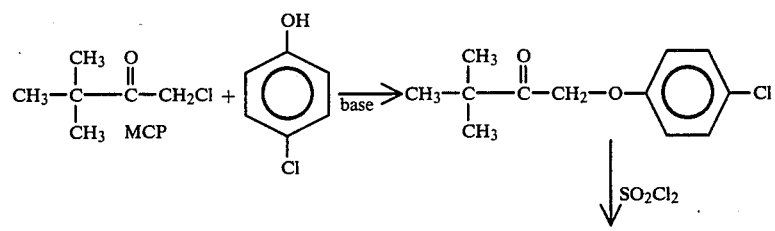

-continued

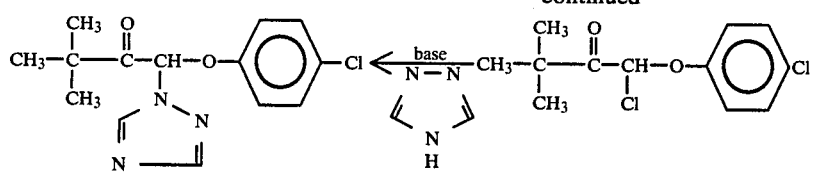

The results obtained were as follows:

|  | Wt. % Dichloro- in Starting Material | |
|---|---|---|
|  | 1 | 4 |
| % Active Ingredient in Product | 98.6 | 93.0 |
| % Net Yield | 99.2 | 95.5 |

It will be understood that the specification and examples are illustrative but not limitative of the present invention and that other embodiments within the spirit and scope of the invention will suggest themselves to those skilled in the art.

What is claimed:

1. In the reaction of pinacolone with chlorine in a solvent to produce monochloropinacolone, the improvement which comprises employing as the solvent methanol which contains HCl at the outset of the reaction whereby the amount of by-product dichloropinacolone produced is reduced.

2. The process according to claim 1, wherein at the end of the reaction the solvent is removed, the solvent containing by-product HCl, and the HCl-containing solvent is employed as solvent in a further cycle.

3. The process according to claim 1, wherein the HCl at the outset of the reaction is present in at least about 500 mol % based on the pinacolone.

4. The process according to claim 1, wherein the HCl at the outset of the reaction is present in about 500 to 700 mol % based on the pinacolone.

5. The process according to claim 1, wherein the solvent is substantially saturated with HCl at the outset of the reaction.

6. In the production of a compound of the formula

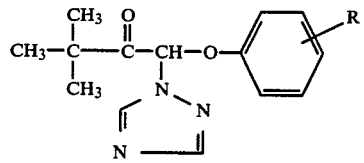

in which R is halogen, phenyl, phenoxy, halophenyl or halophenoxy, by (a) reacting pinacolone with chlorine to produce monochloropinacolone, (b) reacting the monochloropinacolone with a phenol of the formula

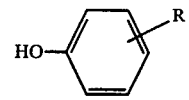

to produce a phenoxypinacolone, (c) halogenating that to produce an α-halo-α-phenoxy-pinacolone, and (d) reacting that with 1,2,4-triazole, the improvement which comprises carrying out (a) in a methanol to which HCl has been added whereby no more than about 1% of dichloropinacolone is produced along with the monochloropinacolone, and directly reacting the monochloropinacolone with the phenol without separation of the dichloropinacolone.

* * * * *